United States Patent [19]

Growdon et al.

[11] 4,346,085

[45] Aug. 24, 1982

[54] PROCESS AND COMPOSITION FOR TREATING DISORDERS BY ADMINISTERING AMPHETAMINE AND CHOLINE

[75] Inventors: John H. Growdon, Brookline; Richard J. Wurtman, Boston, both of Mass.

[73] Assignee: Massachusetts Institute of Technology, Cambridge, Mass.

[21] Appl. No.: 229,812

[22] Filed: Jan. 30, 1981

Related U.S. Application Data

[63] Continuation-in-part of Ser. No. 126,124, Feb. 29, 1980, abandoned, which is a continuation-in-part of Ser. No. 88,227, Nov. 25, 1979, abandoned, which is a continuation of Ser. No. 847,967, Nov. 2, 1977, abandoned.

[51] Int. Cl.³ .............. A61K 31/131; A61K 31/445; A61K 31/685
[52] U.S. Cl. ................................ 424/199; 424/267; 424/330
[58] Field of Search ................. 424/199, 267, 330

[56] References Cited

U.S. PATENT DOCUMENTS 3,947,579  3/1976  Fuxe ................................ 424/247

OTHER PUBLICATIONS

Wurtman et al., The Lancet, Jul. 9, 1977.
Growdon et al., New Eng. Jour. Med., 297 (10): 524 (1977).

*Primary Examiner*—Stanley J. Friedman
*Attorney, Agent, or Firm*—Arthur A. Smith, Jr.; Paul J. Cook

[57] ABSTRACT

Choline or a natural or synthetic compound that dissociates to form choline is administered to a patient concomitantly with a drug in order to potentiate the effect of the drug by increasing acetylcholine levels in the brain or other tissues, and/or to suppress, or block the development of, unwanted side effects of the drug, by increasing acetylcholine levels in the brain or other tissues.

12 Claims, No Drawings

PROCESS AND COMPOSITION FOR TREATING DISORDERS BY ADMINISTERING AMPHETAMINE AND CHOLINE

The Government has rights in this invention pursuant to Grant No. MH-28783 from the National Institute of Mental Health.

REFERENCES TO RELATED APPLICATIONS

This application is a continuation-in-part of Ser. No. 126,124 filed Feb. 29, 1980, abandoned, which, in turn is a continuation-in-part of Ser. No. 088,227, filed Oct. 25, 1979, abandoned, which, in turn, is a continuation of Ser. No. 847,967, filed Nov. 2, 1977, now abandoned.

BACKGROUND OF THE INVENTION

This invention relates to a process and composition for the administration of choline, or natural or synthetic compounds that dissociate to form choline, along with a drug, in order to treat human disorders by increasing acetylcholine levels in brain and other tissues.

There are a number of diseases which affect acetylcholine-containing neurons in the brain or other tissues, and which are treated by drugs that cause undesired side effects by diminishing acetylcholine's release; there also exist diseases now treated by other drugs in which the potency and/or efficacy of the drugs could be improved by combining them with choline or natural or synthetic compounds that dissociate to form choline in order thereby to enhance the release of acetylcholine. Such diseases include both those primarily involving the brain (e.g., diseases of higher cortical functions; psychiatric illnesses; movement disorders) and those involving the peripheral nervous system (e.g., neuromuscular disorders). Tardive dyskinesia is a particularly common movement disorder associated with inadequate release of brain acetylcholine as a result of drug administration for the initial brain disease (e.g., psychosis). Tardive dyskinesia is a choreic movement disorder characterized by involuntary twitches in the tongue, lips, jaw and extremities. It typically occurs in susceptible persons after chronic ingestion of neuroleptic drugs and may involve an imbalance in the postulated reciprocal relation between dopaminergic and cholinergic neurons and the basal ganglions. Thus, drugs that either block catecholamine synthesis (e.g., alpha-methyl-p-tyrosine), deplete the brain of monoamines (e.g., reserpine, tetrabenazine) or antagonize dopamine's actions on synaptic receptors (e.g., phenothiazines, haloperidol) often suppress tardive dyskinesia, whereas drugs that indirectly stimulate dopamine receptors (e.g., emphetamine, levodopa) often exacerbate the abnormal movements. Drugs assumed to increase the amount of acetylcholine within brain synapses (e.g., physostigmine, deanol), also tend to suppress the chorea of tardive dyskinesia, whereas anticholinergics (e.g., scopolamine), make it worse.

We have shown that choline administered by injection or by dietary supplementation increases blood choline levels in the rat; this, in turn, increases choline levels in cholinergic neurons within the brain and elsewhere in the body, thereby accelerating the synthesis of acetylcholine, increasing tissue acetylcholine levels, and increasing the amounts of acetylcholine released into brain synapses. In human beings, oral doses of choline or of lecithin, a naturally-occurring compound that dissociates to choline were found to cause dose-related increases in blood choline levels of sufficient magnitude (based on the studies on rats) to enhance brain acetylcholine synthesis and release; choline levels in the cerebrospinal fluid also rose in parallel. It has also been reported in four human patients that the administration of choline decreased the choreiform movements of tardive dyskinesia; no data were provided as to whether or not the drug given concurrently for psychosis (haloperidol, 3 mg per day) continued to be effective during the brief period of choline administration, and it was concluded that the apparent effectiveness of choline had to be interpreted with caution, since " . . . all four patients with tardive dyskinesia could have been gradually improving during the study" since this disease is characterized by extreme variability of clinical course. Thus, prior to our invention, it had not been known that the concomitant administration of choline or of a natural or synthetic compound that dissociates to form choline along with an anti-psychotic drug that causes tardive dyskinesia as a side effect could significantly reduce or prevent the onset of tardive dyskinesia, without blocking the effectiveness of the drug in treating psychosis.

SUMMARY OF THE INVENTION

This invention is based upon the discovery that choline or a physiologically-acceptable natural or synthetic compound that dissociates to form choline, when administered concomitantly with a drug, can, by increasing neuronal acetylcholine levels, (1) reduce or prevent undesirable side effects of the drug associated with inadequate acetylcholine release, and/or (2) potentiate the effectiveness of the drug. The choline and drug may be administered orally such as in tablet, capsule or liquid form or parenterally by intravenous, intramuscular or subcutaneous injection. The process of this invention is useful even with patients having a prior history of the undesirable side effect or of suboptimal therapeutic response, or of therapeutic responses requiring a very large drug dose, but who continue taking the drug.

DETAILED DESCRIPTION OF SPECIFIC EMBODIMENTS

In accordance with this invention, choline or a compound that dissociates to form choline is orally administered to a patient prior to or together with a drug in order to increase blood levels of choline, and thereby to increase the level of acetylcholine in the brain. The acetylcholine is synthesized from choline and acetyl CoA in a reaction catalyzed by choline acethyltransferase (CAT). It has been found that the administration of choline or a compound that dissociates to form choline potentiates the drug by reducing the incidence or suppressing side effects of the primary drug and/or that lower dosages of the primary drug are needed to attain the desired effects of the drug. While the results obtained will vary from patient to patient, the reduced side effects and increased efficacy observed are sufficiently significant as to justify the conclusion that their reduction is caused by administration of choline or a compound that dissociates to form choline.

There are a number of brain and peripheral diseases involving cholinergic neurons that are presently treated with drugs that are only sometimes effective, or that require very large doses of the drugs (with correspondingly greater cost and incidence of side effects); some of these diseases can be more effectively treated by combining the existing drug therapy with concomitant choline or natural or synthetic compounds that dissociate to form choline. One example is the mania phase of manic-depressive psychoses, which is currently treated with lithium salts. These salts, as a biochemical side effect, interfere with the uptake of choline into the brain; this tends to reduce brain acetylcholine levels, which exacerbates the mania. The co-administration of choline with the lithium salts would allow more effective treatment of the mania, and a reduction in the lithium dose needed by most patients. Another example of myasthenia gravis, a peripheral disease involving the cholinergic nerves that innervate skeletal muscle. The current mode of treatment involves giving drugs like neostigmine (Prostigmin) that increase acetylcholine levels in neuromuscular snyapses by blocking the degradation of this neurotransmitter. Were choline or a natural or synthetic compound that dissociates to form choline to be given concomitantly with the cholinesterase-inhibitor, the resulting increases in acetylcholine levels would both potentiate the effect of the cholinesterase-inhibitor and allow for a reduction in its dose.

Some of the drugs utilized in the present invention are those which cause significant undesirable effects. Representative of such drugs are neuroleptics, such as the phenothiazines including thioridozine (MELLARIL ®), fluphenazine (PROLIXIN ®) trifluoperazine and chlorpromazine (THORAZINE ®); the thioxanthenes including chlorprothixene (TARACTON ®) and thiothixene (NAVANE ®); the butyrophenones including haloperidol (HALDOL ®) and indolic compounds including molindone (MOBAN ®) that are used in the treatment of such diseases as schizophrenia, Huntington's disease and Tourette's syndrome. Other drugs that cause undesired effects include psychomotor stimulants such as amphetamine (DEXADRINE ®), and methylphenidate (RITALIN ®) that are used to treat patients with minimal brain dysfunction, hyperactivity and specific dyslexias.

The effects of some other drugs utilized in this invention are potentiated. Representative of such drugs are: (1) isoxsuprine (VASODILAN ®) and dihydroergotamines (HYDERGINE ®), that are used in the treatment of senility; (2) gluco-cortico-steroids such as triamcinotone (ARISTOCORT ®) and predinsone (METICORTEN ®) and anti-cholinesterase drugs such as neostigmine (PROSTIGMIN ®) and pyridostigmine (MESTINON ®) that are used to treat neuromuscular diseases, including polymyositis and myasthenia gravis; (3) lithium (ESKALITH ®) that is used to treat manic-depressive illness and (4) tranquillizers such as phenobarbitol (LUMINAL ®), and diazepam (VALIUM ®) that are used to treat anxiety psychoneurosis.

The choline can be administered as choline salts, such as the chloride bitartrate or the like, or as a compound that dissociates to choline, such as an acylglycerophosphocholine, e.g., lecithin, lysolecithin, glycerophosphatidyl choline, mixtures thereof or the like. By the term acylglycerophosphocholine as used herein is meant a compound of the formula:

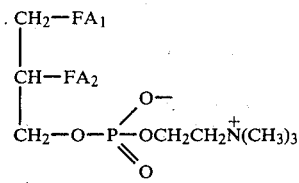

wherein $FA_1$ and $FA_2$ can be the same or different and are fatty acid residues having from 6–26 carbon atoms, usually 16–24 carbon atoms and can be saturated or unsaturated such as palmitic acid, palmitoleic acid, stearic acid, oleic acid, linoleic acid, eicosenoic acid, arachidonic acid, docosahexaenoic acid, eicosapentaenoic acid, linolenic acid, mixtures thereof or the like. The fatty acid residues of the acylglycerophosphocholine can be varied easily by contacting the acyglycerophosphocholine, e.g., a lecithin with phospholipase A1 or A2 (to cleave one fatty acid residue) or then phospholipase B (when desired to cleave both fatty acid residues) and then contacting the cleaved compound with the fatty acid of choice. These choline producing compounds also can be administered to patients having lower than normal plasma choline levels, such as patients experiencing renal dialysis. It is preferred to employ an acyglycerophosphocholine, e.g., lecithin as the choline source since it is not degraded in the gut in contrast to choline. The choline or compound that dissociates to choline is administered so that a choline level of at least about 20–30 nanomoles/ml and usually between about 10 and 50 n moles/ml is attained in the patient's bloodstream. For example, when administering choline chloride in the form of capsules or tablets, suitable dosages are from about 1 to 30 g/day, preferably 3–20 g/day taken in divided doses 500 to 1000 mg/cap or tab. When choline chloride is administered in liquid form admixed with a conventional liquid carrier such as a sweetened elixir or the like, from about 1 to 10 grams/15 ml, preferably from about 2 to 5 grams/15 ml can be utilized. When utilizing lecithin in a liquid carrier, it is administered in amounts of between about 0.1 and 50 grams/day. When lecithin is administered in granular form, as a tablet or in a capsule, it is employed in amounts of between about 0.1 and 100 g/day, usually between about 30 and 50 g/day. Normally, lecithin is not available as a pure compound and is available in admixture with other phospholipids wherein the lecithin comprises about 20–30 weight percent of the mixture.

In the process of this invention, the choline or compound that dissociates to choline is administered prior to or concomitantly with the drug. When administered prior to the drug, the period of time between choline administration and drug administration must be less than when acetylcholine concentration reduction begins to occur in the brain. Generally, the period of time between administrations is less than about 36 hours, preferably less than about 24 hours.

The following example illustrates the present invention and is not intended to limit the same.

EXAMPLE I

This example illustrates that choline significantly reduces tardive dyskinesia in patients taking antipsychotic drugs.

20 subjects were selected at random from a large group of inpatients with stable chronic buccal-lingual-masticatory dyskinesia. Each patient has received phenothiazines or haloperidol in the past, and 13 were still taking such drugs when the study began (Table I). Anticholinergic medications (benztropin or trihexyphenidyl) were discontinued during the study, but the doses of all other medications, including neuroleptics, were unchanged.

The severity of the chorea was illustrated by counting the number of eye blinks, tongue protrusions, slow tongue movements inside the mouth, jaw closures or lip movements visible during a 30-second interval. Each patient sat in a quiet private room with 3 observers, one of whom was present during all examinations. Two observers counted the movements independently on two separate days before the study began and made subsequent counts every three days thereafter. The mean counts were tabulated during the control periods, the second week of choline and the second week of placebo ingestion and scored the percentage change as follows: −25 to +25 percent, no change (i.e., falling within the anticipated day-to-day variation); 25 to 50 percent, moderately changed; and >50 percent greatly changed.

Choline chloride (150 mg per kilogram per day during the first week and 200 mg per kilogram per day during the second week) was mixed in a sweet commercial beverage and dispensed in three daily divided doses. The placebo, sucrose octa acetate, was also dissolved in the beverage (10 mg per liter) and administered in the same manner and volume as the choline. Both solutions tasted bitter, but the placebo did not impart the "fishy" odor sometimes noted in patients who chronically ingest choline.

Half the patients received choline, and the other half placebo, for two weeks; these schedules were reversed after a 10-day interval during which neither choline nor placebo was dispensed.

Blood samples for choline measurements were collected from every patient before the drug trial began and on three subsequent occasons: during the second week of therapy, on the ninth day of the drug-free interval and during the second week of the crossover period (the final two weeks of therapy) all blood samples were collected before breakfast. During the treatment periods, they were obtained one hour after the subjects ingested the beverage. Serum samples were separated, frozen and assayed for choline content by a conventional radio-enzymatic method.

The chemical characteristics of the 20 patients with tardive dyskinesia are set forth in Table I.

TABLE I

| Case No. | Age yr. | Sex | Primary Diagnosis | Severity of Tardive Dyskinesia | Current Medication | Dosage mg/day |
|---|---|---|---|---|---|---|
| 1 | 36 | F | Schizophrenia | Moderate | Thiothixene | 100 |
| 2 | 55 | F | Schizophrenia | Moderate | Chlorpromazine | 300 |
|   |    |   |               |          | Trifluoperazine | 40 |
| 3 | 38 | F | Schizophrenia | Moderate | Haloperidol | 15 |
|   |    |   |               |          | Phenytoin | 300 |
|   |    |   |               |          | Phenobarbital | 100 |
| 4 | 75 | F | Senile dementia | Severe | Thioridazine | 75 |
| 5 | 63 | M | Schizophrenia | Severe | Phenytoin | 300 |
| 6 | 85 | F | Senile dementia | Severe | Diazepam | 8 |
|   |    |   |               |          | Phenytoin | 300 |
| 7 | 79 | F | Schizophrenia | Moderate | None | — |
| 8 | 66 | F | Mental retardation with psychosis | Severe | Phenytoin | 300 |
| 9 | 73 | F | Schizophrenia | Severe | None | — |
| 10 | 48 | F | Schizophrenia | Severe | Haloperidol | 5 |
|   |    |   |               |          | Phenobarbital | 120 |
| 11 | 72 | F | Schizophrenia | Moderate | Chlorprothizene | 150 |
| 12 | 80 | F | Schizophrenia | Severe | Thioridazine | 50 |
|   |    |   |               |          | Diphenhydramine | 100 |
| 13 | 63 | F | Schizophrenia | Mild | Thioridazine | 300 |
| 14 | 52 | F | Schizophrenia | Mild | Chlorpromazine | 100 |
|   |    |   |               |          | Phenytoin | 300 |
|   |    |   |               |          | Phenobarbital | 100 |
| 15 | 62 | F | Schizophrenia | Moderate | None | — |
| 16 | 37 | M | Schizophrenia | Mild | Fluphenazine | 25 |
| 17 | 76 | M | Senile dementia | Severe | Diphenhydramine | 50 |
| 18 | 32 | M | Mental retardation with psychosis | Moderate | Haloperidol | 40 |
|   |    |   |               |          | Phenytoin | 300 |
| 19 | 37 | F | Mental retardation with psychosis | Severe | Phenytoin | 300 |
|   |    |   |               |          | Phenobarbital | 160 |
| 20 | 66 | M | Schizophrenia | Mild | Thioridazine | 400 |

Before treatment, plasma choline levels ranged between 8.6 and 20.5 nmol per milliliter (12.4±1.0, mean±S.E.M.). During the second week of choline ingestion (200 mg per kilogram per day), plasma choline levels in blood obtained one hour after a choline does increased in all patients and ranged between 18.2 and 60.1 nmol per milliliter (33.5±2.5, mean±S.E.M., a 170 percent increase; $P<0.001$ by Student's t-test). Plasma choline levels measured during placebo administration and at the end of the 10-day "washout" period did not differ significantly from control levels.

Buccal-lingual-masticatory movements lessened in nine patients during the period of choline administration; five patients during the period of choline administration improved greatly and four improved moderately (Table II).

TABLE II

Clinical Effect of Choline Administration on the Bucal-Lingual-Masticatory Movements in 20 Patients with Tardive Dyskinesia

| Classification | No. of Patients | Mean No. of Movements/ 30 Sec | | % Change Range |
|---|---|---|---|---|
| | | Before Choline | During Choline | |
| Greatly improved | 5 | 12.6 | 4.2 | +74–+84 |
| Moderately improved | 4 | 21.2 | 11.7 | +41–+55 |
| Unchanged | 10 | 13.4 | 13.6 | +18– −21 |
| Worsened | 1 | 4.5 | 27.5 | −511 |

*+ indicates improvement and − worsening of the chorea

Case 1 had rapid, tremulous tongue movements, which virtually ceased during choline therapy. Cases 2 and 3 had slower, rolling tongue movements within the mouth; these movements, too, were greatly suppressed during choline treatment, but not during placebo administration.

Tongue movements also decreased markedly, but not completely, in two patients with more severe dyskinesia. Case 4 protruded her tongue ("serpent's tongue") 20 times per 30 seconds during the initial observation period. In the final week of choline therapy, the rate decreased to five times per 30 seconds, although the tongue continued to roll inside her mouth. (Placebo ingestion had no effect on the rate of tongue protrusions.) Two weeks after she stopped taking choline, her tongue protrusions returned to their pretreatment rate of 20 per 30 seconds. Within a week of the beginning of a second course of choline treatment (200 mg per kilogram per day), the rate of tongue protrusions again decreased to six times per 30 seconds.

Case 5 protruded his tongue 20 to 30 times per 30 seconds during initial observations but did not protrude it at all during the second week of choline ingestion. It continued to move inside his mouth, but the movement frequency decreased by 49 percent.

Buccal-lingual-masticatory movements decreased moderately (25 to 50 percent) in another four subjects. Cases 6 and 7 had fewer jaw movements during choline ingestion, but their tongue motions did not change. The number of jaw movements also diminished during choline therapy in Case 8, although the frequency of her eye blinks did not change. Tongue and lip movements decreased during choline ingestion in Case 9, but jaw movements were unaffected.

The frequency of tongue movements increased markedly in Case 20 (from four to 27 times per 30 seconds) during the period of choline ingestion, but returned to control counts when the choline was discontinued. Neither choline nor placebo altered buccal-lingual-masticatory movements in the remaining 10 patients.

Another patient with severe akathisia was included in the study; she did not exhibit facial chorea, however, and is not listed in the tables. She was unable to sit still and moved her feet 30 times every 30 seconds. These movements were not altered during placebo ingestion but nearly ceased during choline administration.

No serious side effects were encountered in any subject during the course of the study. Cases 2 and 3 were more withdrawn than usual and possibly depressed during choline treatment. Three patients (Cases 4, 7 and 15) experienced symptoms of mild cholinergic toxicity, including lacrimation, blurred vision, anorexia and diarrhea, while taking 200 mg of choline per kilogram per day. All the effects were dose related and subsided when the dosage was reduced.

The patients who participated in the study all exhibited permanent buccal-lingual-masticatory characteristic of tardive dyskinesia and all had taken neuroleptics in the past (although these drugs had been discontinued in seven patients before the study began). Most subjects were elderly women who had taken neuroleptics for many years; the drugs and doses listed in Table I are minimal estimates. Since the onset of tardive dyskinesia was documented only in Case 13, it is possible that some patients in the series had senile chorea, or the mannerisms of mentally retarded or psychotic patients, and not true drug-induced tardive dyskinesia. The variety of their responses to choline (nine better, one worse and 10 unchanged) suggests that the patient sample was indeed heterogeneous at least in the involvement of cholinergic mechanisms. This confusion about causes will remain a problem until an accurate diagnostic test for tardive dyskinesia is found.

Most attempts to treat tardive dyskinesia are based on the theory that neuroleptic drugs, by blocking intrasynaptic dopamine receptors, cause a reflex overactivity of dopaminergic neurons, which may be due to increased dopamine turnover or to "denervation" supersensitivity. Either action would excessively suppress striatal cholinergic neurons (which receive inhibitory impulses from the dopaminergic nigrostriatal pathway) at times of day when the blockade of dopamine receptors was incomplete. Although no therapy is completely satisfactory, numerous efforts to treat stable tardive dyskinesia have employed drugs thought to decrease the amount of dopamine released into central synapses. Other therapeutic strategies designed to increase cholinergic tome at the next synapse distal to that employing dopamine have had only limited success.

Buccal-lingual-masticatory movements decreased in nine patients during the period of choline consumption, but were unaffected by the placebo. The occurrence of cholinergic side effects in three of the subjects provides additional indirect evidence that exogenous choline enhances neuronal acetylcholine synthesis and release in human beings and probably accounts for the suppression of chorea in the nine patients who improved during choline therapy. The buccal-lingual-masticatory movements of these patients were not sufficiently different from those displayed by the group as a whole to permit identification of particular movements that might be especially responsive to choline treatment.

The mean blood choline levels, both before and during treatment, in the patients who responded to choline did not differ significantly from the mean of the group as a whole—in nine responders, 13.1±1.4 nmol per milliliter before and 31.5±2.5 during treatment, and in the entire group, 12.4±1.0 nmol per milliliter before and 33.5±2.5 during treatment—nor did their age (63.3 years vs. 59.8 years) sex (predominantly women), primary diagnosis (predominantly schizophrenia), or concurrent neuroleptic medication (Table I).

Oral doses of lecithin, the major source of dietary choline, may be an alternate way to treat patients with tardive dyskinesia. We observe that lecithin administration, like that of free choline, elevates blood choline levels in human subjects.

We claim:

1. A composition of matter comprising (a) a drug which, when administered to a human causes side effects associated with inadequate release of brain acetylcholine, said drug being selected from the group consisting of amphetamine and methylphenidate and (b) an amount of a compound effective to raise the bloodstream choline level of a patient to between about 10 and 50 nanomoles/ml and to release adequate amounts of brain acetylcholine selected from the group consisting of choline, a salt of choline, lysolecithin, an acyglycerophosphocholine having the formula:

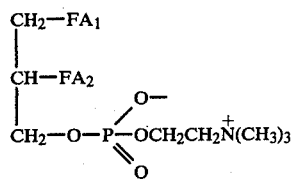

wherein $FA_1$ and $FA_2$ can be the same or different and are fatty acid residues having from 6–26 carbon atoms, glycerophosphatidyl choline and mixtures thereof.

2. The composition of claim 1 wherein the compound is acyglycerophosphocholine.

3. The composition of claim 2 wherein the acyglycerophosphocholine is lecithin.

4. The composition of claim 1 wherein the compound is choline chloride.

5. The composition of any one of claims 1, 2, 3 or 4 wherein the drug is amphetamine.

6. The composition of any one of claims 1, 2, 3 or 4 wherein the drug is methylphenidate.

7. The process of reducing or eliminating undesirable side effects of a drug administered to a human having a neurologic disorder, which side effects result from inadequate release of brain acetylcholine, said drug being selected from the group consisting of amphetamine and methylphenidate, which comprises administering concomitantly with the drug an amount of a compound effective to raise the bloodstream choline level of a patient to between about 10 and 50 nanomoles/ml and to release adequate amounts of brain acetylcholine selected from the group consisting of choline, a salt of choline, lysolecithin, an acyglycerosphosphocholine, having the formula:

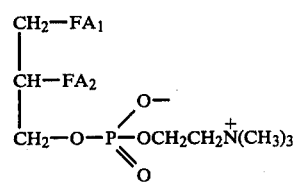

wherein $FA_1$ and $FA_2$ can be the same of different and are fatty acid residues having from 6–26 carbon atoms, glycerophosphatidyl choline and mixtures thereof.

8. The process of claim 7 wherein the drug and the compound are administered together as a capsule or tablet.

9. The process of claim 7 wherein the drug and the compound are administered together in a liquid.

10. The process of claim 7 wherein the compound is an acyglycerophosphocholine.

11. The process of claim 7 wherein the compound is choline chloride.

12. The process of claim 7 wherein the acyglycerophosphocholine is lecithin.

* * * * *